United States Patent [19]

Scherm et al.

[11] 4,051,143

[45] Sept. 27, 1977

[54] PROCESS FOR THE PRODUCTION OF α-[2-(P-CHLOROPHENOXY)-ISOBUTYRYL]-β-NICOTINOYL GLYCOL ESTER

[75] Inventors: Arthur Scherm, Bad Homburg; Dezsö Peteri, Hammersbach, Marköbel, both of Germany

[73] Assignee: Merz & Co., Germany

[21] Appl. No.: 750,594

[22] Filed: Dec. 15, 1976

Related U.S. Application Data

[63] Continuation of Ser. No. 610,185, Sept. 4, 1975, abandoned.

[30] Foreign Application Priority Data

Sept. 5, 1974 United Kingdom .............. 38778/74

[51] Int. Cl.$^2$ ............................................. C07D 213/55
[52] U.S. Cl. ................. 260/295.5 R; 424/266
[58] Field of Search .................................. 260/295.5 R

[56] References Cited

U.S. PATENT DOCUMENTS 3,723,446  3/1973  Scherm et al. ................ 260/295.5 R

FOREIGN PATENT DOCUMENTS

M6,975  7/1969  France .......................... 260/295.5 R

OTHER PUBLICATIONS

Scherm et al., Chem. Abstracts, vol. 78(25), i59451e, June 25, 1973.

*Primary Examiner*—Alan L. Rotman
*Attorney, Agent, or Firm*—Gordon W. Hueschen

[57] ABSTRACT

The application discloses a novel improved process for the production of α-[2-(p-chlorophenoxy)-isobutyl]-β-nicotinoyl glycol ester, a known compound having a lipid-lowering effect, by the reaction of α-[2-chlorophenoxy)-isobutyryl]-β-ethyl chloride ester with an alkali salt of nicotinic acid, preferably sodium nicotinate, preferably in a high-boiling polar or dipolar aprotic solvent, especially dimethylformamide, most preferably at a temperature of about 120° – 180° C., and most advantageously in refluxing dimethylformamide. An unpredictable increase in yields of the desired product over yields attainable by previously-available processes is thereby obtained.

7 Claims, No Drawings

PROCESS FOR THE PRODUCTION OF α-[2-(P-CHLOROPHENOXY)-ISOBUTYRYL]-β-NICOTINOYL GLYCOL ESTER

This is a continuation of application Ser. No. 610,185, filed Sept. 4, 1975 now abandoned.

The present invention relates to a process for the production of α-[2-(p-chlorophenoxy)-isobutyryl]-β-nicotinoyl glycol ester. α-[2-(p-chlorophenoxy)-isobutyryl]-β-nicotinoyl glycol ester is a known chemical compound which melts at 47° C. As a component of pharmaceutical preparations, α-[2-(p-chlorophenoxy)-isobutyryl]-β-nicotinoyl glycol ester has a lipidlowering effect in the case of hyperlipoidemiae and in the case of increased triglyceride and cholesterol values. Clinical tests have shown that with an intake of 300 mg of α-[2-(p-chlorophenoxy)-isobutyryl]-β-nicotinoyl glycol ester per patient per day, there was significant decrease in the content of cholesterol, triglyceride, phosphatides and free fatty acids in the blood of the patients.

A process for the production of α-[2-(p-chlorophenoxy)-isobutyryl]-β-nicotinoyl glycol ester is already known. According to German Pat. No. 1 941 217, 2-(p-chlorophenoxy)-isobutyric acid is reacted with an ethylene glycol excess in the presence of catalytic quantities of phosphoric acid and p-toluenesulphonic acid to give a semi-ester, and this semi-ester is caused to react with an excess of nicotinic acid chloride in tetrahydrofuran during cooling with ice. After the re-crystallization from acetic acid, a 70 % yield of α-[2-(p-chlorophenoxy)-isobutyryl]-β-nicotinoyl glycol ester hydrochloride having a melting point of 100° C is obtained.

Although this known process leads to useful yields of the desired compound, it does have certain disadvantages. The nicotinic acid chloride, which is caused to react with the semi-ester, constitutes a compound which is sensitive to hydrolysis and for this reason the reaction must be carried out under conditions from which moisture is excluded. Moreover, during this reaction free hydrochloric acid is produced, which makes special demands of the resistance to corrosion of the apparatus used.

The object of the present invention is to provide an improved process for the production of α-[2-(p-chlorophenoxy)-isobutyryl]-β-nicotinoyl glycol ester, which substantially precludes the above mentioned disadvantges and leads to an improved yield of the desired product.

According to the present invention there is provided a process for the production of α-[2-(p-chlorophenoxy)-isobutyryl]-β-nicotinoyl glycol ester in which [2-(p-chlorophenoxy)-isobutyryl]-β-chloroethyl ester is reacted with an alkali metal salt of nicotinic acid. Under the reaction conditions which are provided in accordance with the invention, the desired ester is produced in yields of 90 to 95 %.

To the expert it is surprising that practically no quaternisation of the pyridine nitrogen occurs during the reaction of the higher alkyl chloride [2-(p-chlorophenoxy)-isobutyryl]-β-chloroethyl ester with the pyridine derivative, nicotinic acid salt, since it is known from the Handbook of Synthetic Medicines (SYNTHETISCHE ARZNEIMITTEL), edited by Dr. W. Knoblock, Akademie-Verlag, Berlin 1961, page 531, that during the reaction of pyridine with cetyl chloride or another higher alkyl chloride, it is cetylpyridiumchloride which is chiefly obtained. Therefore, it is surprising that practically no alkylation of the pyridine nitrogen occurs during the reaction provided, in accordance with the invention, of [2-(p-chlorophenoxy)-isobutyryl]-β-chloroethyl ester with an alkali salt of nicotinic acid, but that the desired α-[2-(p-chlorophenoxy)-isobutyryl]-β-nicotinoyl glycol ester is obtained in yields of 90 to 95 %.

In the process according to the invention the sodium salt of nicotinic acid (Na-nicotinate) is preferably used although other alkali metal salts, such as Li-nicotinate or K-nicotinate, are also suitable. The reaction is preferably carried out in a polar or dipolar aprotic solvent having a boiling point between about 100° C and 200° C; solvents which can be used for this purpose are tetrahydrofuran, dimethylformamide and dimethylsulphoxide, dimethylformamide being especially preferred since in that instance the best yields of α-[2-(p-chlorophenoxy)-isobutyryl]-β-nicotinoyl glycol ester are obtained. The process according to the invention is carried out at quite a high temperature. Temperatures of 120° to 180° C are especially suitable for the reaction in a polar or dipolar aprotic solvent solution of the starting reaction materials provided. At these temperatures, approximately 20 to 200 minutes reaction duration is needed for a virtually complete reaction, even shorter times leading to a satisfactory reaction when the reaction temperatures are higher.

The process of the invention for the production of α-[2-(p-chlorophenoxy)-isobutyryl]-β-nicotinoyl glycol ester leads to particularly good yields when [2-(p-chlorophenoxy)-isobutyryl]-chloroethyl ester is reacted with Na-nicotinate for 30 to 120 minutes in boiling dimethylformamaide. At the same time approximately 5 % of dimethylformamide is advantageously removed by distillation from the boiling dimethylformamide, so as to rid the reaction mixture of volatile impurities which have formed. When the reaction has ended, the reaction mixture is cooled to room temperature and the sodium chloride which has formed is filtered off, then washed several times with small quantities of dimethylformamide. The washing dimethylformamide is combined with the reaction solution and the dimethylformamide is then completely removed therefrom by distillation at a moderately high temperature in vacuum. The raw α-[2-(p-chlorophenoxy)-isobutyryl]-β-nicotinoyl glycol ester which then remains and which is virtually free of dimethylformamide, is dissolved in isopropanol, is stirred in boiling isopropanol for approx. 40 to 120 minutes after the addition of a bleaching agent, and the bleaching agent is subsequently filtered from the hot solution. The warm filtered solution containing the desired product is then mixed in a ratio of approx. 1 : 1 with cold isopropanol and the crystallization of the desired ester commences. After approx. 6 to 10 hours at 6° to 8° C the desired product has largely crystallized out and the crystalline pulp is spun off, comminuted and dried. A 70 to 75% yield of α-[2-(p-chlorophenoxy)-isobutyryl]-β-nicotinoyl glycol eter is hereby obtained in the form of a white to pale yellow product. During re-processing of the mother liquor, up to a further approximately 20 % of ester is isolated so that using the process of the invention a total yield of approx. 90 to 95 % is achieved.

The reactants, solvents and adjuvants used in the process according to the invention are, on the whole, easily accessible starting materials and are commercially obtainable. If [2-(p-chlorophenoxy)-isobutyryl]-β-chloroethyl ester should not be available in the required quantity and/or purity, then this ester may for example be obtained quite easily from chloroethanol and p-chlorophenoxy-isobutyric acid. For example, 4 mols of chloroethanol may be heated to approx. 100° C with 1 mol of p-chlorophenoxy-butyric acid in the presence of catalytic quantities of boron trifluoride (approx. 5 %, referred to the acid), and caused to react at this temperature within 50 to 60 minutes. The excess chloroethanol is then removed by distillation, the residue is absorbed into chloroform and washed several times with 10 % $NaHCO_3$ solution. Fractional distillation is then effected; it is possible for the [2-(p-chlorophenoxy)-isobutyryl]-$\beta$-chloroethyl ester to be distilled in water jet vacuum without decomposing. Boiling point 181° C/13 Torr.

The invention will now be further descibed with reference to the following example.

EXAMPLE 8,310 kg of [2-(p-chlorophenoxy)-isobutyryl]-$\beta$-chloroethyl ester, 4,350 kg of Na-nicotinate and 60,000 liters of dimethylformamaide are placed in a reaction flask provided with stirring means and a column, and whilst being stirred and heated to 150 to 155° C, are caused to react within 60 minutes. During the course of the reaction 3 liters of dimethylformamide are removed under normal pressure by way of the distillation column. When the reaction has ended, the residue is cooled to room temperature and the solid salt which has separated out is removed by filtration. Subsequent washing of the filter cake is effected with approx. 8 liters of dimethylformamide.

The filtrate is subjected to vacuum distillation at 15 to 20 torr, approx. 60 liters of dimethylformamide being removed during this process. The distillation residue is stirred under reflux with 5 liters of isopropanol and 0,5 kg of active carbon for a period of 60 minutes, and is then filtered in a pressure filter. The filter cake is subsequently washed with approx. 2 liters of isopropanol. Finally, the filtrate is mixed with 3 liters of cold isopropanol and caused to crystallize at 10° C.

After standing overnight, the reaction product is centrifuged and is dried in a vacuum drying cabinet at 30° C. In the next batch the mother liquor is used instead of the isopropanol.

Approx. 10 kg of $\alpha$-[2-(p-chlorophenoxy)-isobutyryl]-$\beta$-nicotinoyl glycol ester having a melting point of 46° C to 48° C is obtained (91 % of theory).

The product has the following analytical characteristics:

| C: | calculated: | 59.40 %, | found: | 59.22 % |
|----|-------------|----------|--------|---------|
| H: | " | 4.95 %, | " | 4.98 % |
| Cl: | " | 9,80 %, | " | 9.59 % |
| N: | " | 3.85 %, | " | 3.88 % |

The $\alpha$-[2-(p-chlorophenoxy)-isobutyryl]-$\beta$-nicotinoyl glycol ester produced in accordance with the invention is a pale yellow, crystalline powder, which can be used as active agent in pharmaceutical preparations. Both in human beings and in animals oral administration, e.g. in the form of tablets, lozenges, soft gelatin capsules and hard gelatin capsules leads to a significant reduction in the content of cholesterol, triglyceride phosphatides and free fatty acids in the blood. $\alpha$-[2-(p-chlorophenoxy)-isobutyryl]-$\beta$-nicotinoyl glycol ester can also be worked into such tablets, lozenges and capsules, which release the active agent after a time-lag. A suitable medicine which is to be used orally may for example consist of gelatin capsules each of which contains 300 mg of $\alpha$-[2-(p-chlorophenoxy)-isobutyryl]-$\beta$-nitotinoyl glycol ester in 245 mg of wax mixture.

What we claim is:

1. A process for the production of $\alpha$-[2-(p-chlorophenoxy)-isobutyryl]-$\beta$-nicotinoyl glycol ester in high yields which consists essentially of reacting [2-(p-chlorophenoxy)-isobutyryl]-$\beta$-chloroethyl ester with an alkali metal salt of nicotinic acid in a polar or dipolar aprotic solvent having a boiling point between about 100° C. and 200° C.

2. A process as claimed in claim 1 in which [2-(p-chlorophenoxy)-isobutyryl]-$\beta$-chloroethyl ester is reacted with sodium nicotinate.

3. A process as claimed in claim 1 in which the solvent is dimethylformamide.

4. A process as claimed in any one of claim 1 which is carried out at temperatures of 120° to 180° C.

5. A process as claimed in any one of claim 1 in which the reaction is carried out for period of 20 to 200 minutes.

6. A process as claimed in claim 5 in which [2-(p-chlorophenoxy)-isobutyryl]-$\beta$-chloroethyl ester is reacted with Na-nicotinate for 30 to 120 minutes in boiling dimethylformamide.

7. Process as claimed in claim 6 in which at the end of the reaction the dimethylformamide is largely separated out by distillation and the residue is caused to crystallize from isopropanol.

* * * * *

UNITED STATES PATENT OFFICE
CERTIFICATE OF CORRECTION

Patent No. 4,051,143         Dated Sept. 27, 1977

Inventor(s) Scherm et al

It is certified that error appears in the above-identified patent and that said Letters Patent are hereby corrected as shown below:

Col. 2, line 58: "eter" should read --ester--
Col. 4, line 23: "nitotinoyl" should read -- nicotinoyl --.

Signed and Sealed this

Second Day of May 1978

[SEAL]

Attest:

RUTH C. MASON
Attesting Officer

LUTRELLE F. PARKER
Acting Commissioner of Patents and Trademarks